(12) United States Patent
Grice et al.

(10) Patent No.: US 10,085,725 B2
(45) Date of Patent: Oct. 2, 2018

(54) PHANTOM DESIGN FOR TESTING OF DOPPLER ULTRASOUND FUNCTION

(71) Applicant: Vanderbilt University, Nashville, TN (US)

(72) Inventors: Jared V. Grice, Nashville, TN (US); Ronald R. Price, Franklin, TN (US); David R. Pickens, III, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 150 days.

(21) Appl. No.: 15/153,531

(22) Filed: May 12, 2016

(65) Prior Publication Data

US 2017/0325787 A1    Nov. 16, 2017
US 2018/0193001 A9    Jul. 12, 2018

Related U.S. Application Data

(60) Provisional application No. 62/160,050, filed on May 12, 2015.

(51) Int. Cl.
  *A61B 8/00*  (2006.01)
  *A61B 8/08*  (2006.01)

(52) U.S. Cl.
  CPC .............. *A61B 8/587* (2013.01); *A61B 8/488* (2013.01)

(58) Field of Classification Search
  CPC ................................ A61B 8/587; A61B 8/488
  USPC ....... 141/250, 266, 270, 271, 311; 73/866.4, 73/1.83, 1.86, 865.6; 137/563, 571
  See application file for complete search history.

(56) References Cited

U.S. PATENT DOCUMENTS

| | | | | |
|---|---|---|---|---|
| 2,674,118 A | * | 4/1954 | Westmoreland ....... | G01N 11/06 374/135 |
| 2,990,623 A | * | 7/1961 | Keyser, Jr. ............. | G01C 19/38 137/571 |
| 3,520,329 A | * | 7/1970 | Weber .................... | B60K 15/03 137/571 |
| 3,610,220 A | * | 10/1971 | Yamada ........... | B60K 15/03504 123/518 |

* cited by examiner

*Primary Examiner* — Robert R Raevis
(74) *Attorney, Agent, or Firm* — Nixon Peabody LLP; Eduardo J. Quiñones

(57) ABSTRACT

A Doppler phantom includes a first reservoir, a second reservoir, a fluid line coupling the first and second reservoirs, a pressure line coupling the first and second reservoirs, and a tissue mimicking material surrounding at least the fluid line. The phantom can be positioned in first and second positions, where the first reservoir defines an elevated reservoir and the second reservoir defines a lower reservoir in the first position, where the second reservoir defines the elevated reservoir and the first reservoir defines the lower reservoir in the second position. The fluid line provides a path for fluid to travel from the elevated reservoir to the lower reservoir via gravity in either of the first or second positions, and the pressure line provides a path for gas to transfer from the lower reservoir to the elevated reservoir while the fluid travels in either of the first or second positions.

8 Claims, 16 Drawing Sheets

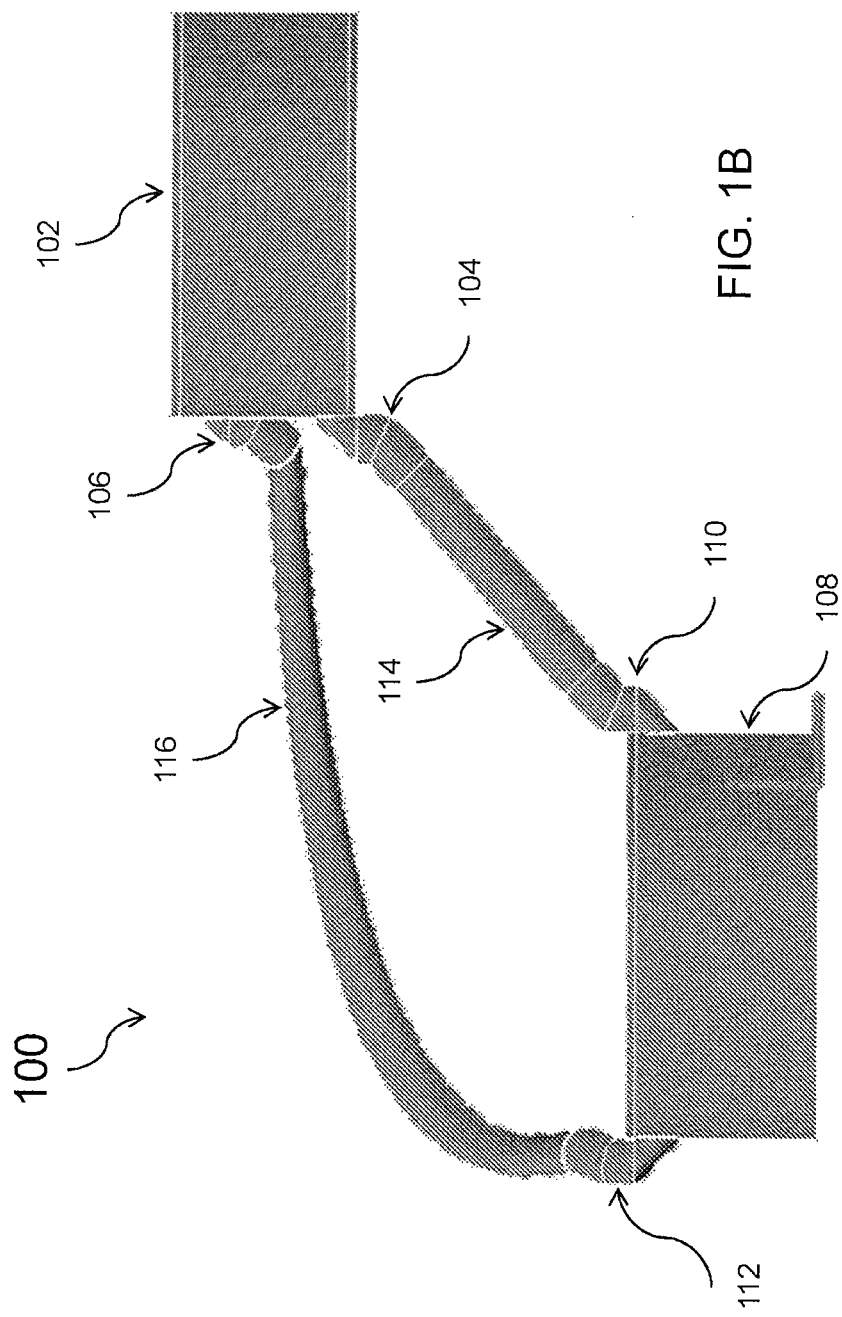

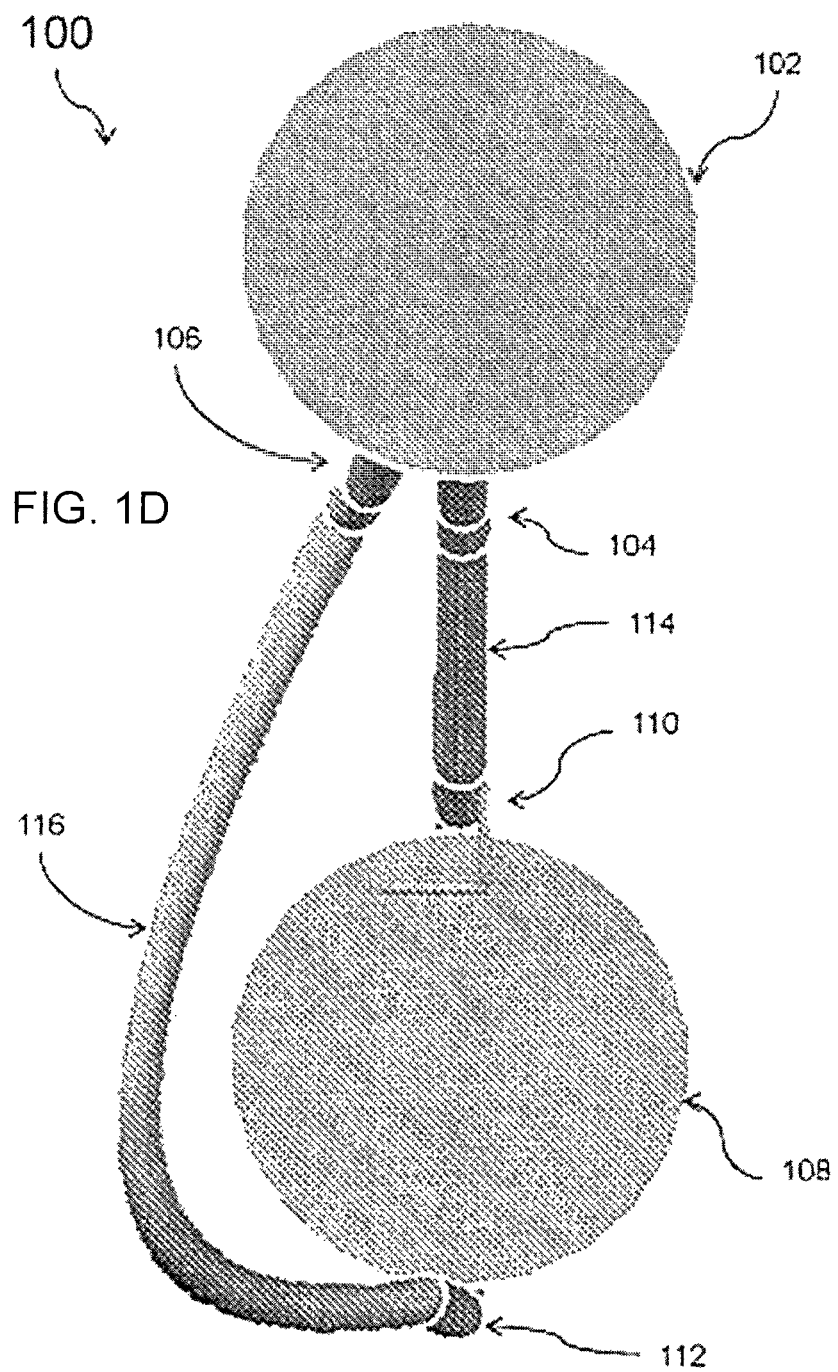

PHANTOM DESIGN FOR TESTING OF DOPPLER ULTRASOUND FUNCTION

CROSS-REFERENCE TO RELATED APPLICATIONS

This application claims priority to and the benefit of U.S. Provisional Patent Application No. 62/160,050, filed May 12, 2015, the contents of which are hereby incorporated by reference in their entirety as if fully set forth herein.

FIELD OF THE INVENTION

The present invention relates to testing of Doppler ultrasound function, and more specifically to apparatus and methods for using such apparatus in routine quality testing of Doppler ultrasound function.

BACKGROUND

Doppler ultrasound is one of the most widely used medical imaging procedures. Even though Doppler ultrasound is commonplace in hospitals and clinics, there may be considerable heterogeneity in system performance between different devices. Therefore, testing of system performance and stability is critical. The generally accepted approach for verifying system performance and stability is to use a standard test device, commonly referred to as a phantom.

With regards to phantom design, there are two main phantom types. The first type uses a filament (string) driven by a motor and running on a set of pulleys. The filament is moved under water in a reservoir and a measuring transducer is placed in contact with the surface of the water to visualize the flow. The second phantom type uses blood-mimicking fluid in a simulated blood vessel, instead of a filament, while a pump creates controlled flow that can be imaged by the Doppler ultrasound system under test. These types of commercially available phantoms require a motor and external power and can be bulky, expensive, or require lengthy set-up times.

SUMMARY

Embodiments of the invention concern apparatus and methods for testing of Doppler ultrasound function. In a first embodiment of the invention, a Doppler phantom is provided. The phantom includes a first reservoir, a second reservoir, a fluid line coupling the first reservoir and the second reservoir, a pressure line coupling the first reservoir and the second reservoir, and a tissue mimicking material surrounding at least the fluid line. The phantom can be positioned in at least a first position and a second position, where the first reservoir defines an elevated reservoir and the second reservoir defines a lower reservoir in the first position and where the second reservoir defines the elevated reservoir and the first reservoir defines the lower reservoir in the second position. In this spatial definition, the two reservoirs define a pressure gradient created by gravity from an elevated reservoir to a lower reservoir. The fluid line defines a path for fluid to travel from the elevated reservoir to the lower reservoir via gravity in either of the first position or the second position. The pressure line defines a path for gas to transfer from the lower reservoir to the elevated reservoir while the fluid travels in either of the first position or the second position.

In the phantom, each of the first reservoir and the second reservoir can be cylindrical and parallel with each other.

Further, each reservoir of the first reservoir and the second reservoir can includes a fluid port coupling the fluid line to each reservoir and a pressure port coupling the pressure line to each reservoir. The fluid port for each reservoir can arranged so as to be at a bottommost portion in the elevated reservoir with respect to gravity and at a topmost portion in the lower reservoir with respect to gravity. The pressure port for each reservoir can be arranged so as to be at a topmost portion in the elevated reservoir with respect to gravity and at a topmost portion in the lower reservoir with respect to gravity.

The fluid line can be configured to travel a direct path between the first reservoir and the second reservoir.

Also, at least one of the first reservoir or the second reservoir can include an access port.

Additionally, each of the first position and the second position can be obtained by rotating the phantom by 90 degrees from another of the first position and the second position.

In a second embodiment, an apparatus is provided that includes a first reservoir, a second reservoir, a fluid line, and a pressure line. In the apparatus, the first reservoir defines an elevated reservoir and the second reservoir defines a lower reservoir in a first position of the apparatus and the second reservoir defines the elevated reservoir and the first reservoir defines the lower reservoir in a second position of the apparatus. The fluid line defines a path for fluid to travel from the elevated reservoir to the lower reservoir via gravity and the pressure line defines a path for gas to transfer from the lower reservoir to the elevated reservoir while the fluid travels.

In the second embodiment, each of the first reservoir and the second reservoir can be substantially cylindrical.

Further, each reservoir of the first reservoir and the second reservoir can include a fluid port coupling the fluid line to each reservoir and a pressure port coupling the pressure line to each reservoir. The fluid port for each reservoir can be arranged so as to be at a substantially bottommost portion in the elevated reservoir with respect to gravity and at a substantially topmost portion in the lower reservoir with respect to gravity. The pressure port for each reservoir can be arranged so as to be at a substantially topmost portion in the elevated reservoir with respect to gravity and at a substantially topmost portion in the lower reservoir with respect to gravity. Also, the fluid line can be configured to travel a substantially direct path between the first reservoir and the second reservoir.

Also, at least one of the first reservoir or the second reservoir can include an access port.

Additionally, each of the first position and the second position can be obtained by rotating the apparatus by approximately 90 degrees from another of the first position and the second position.

BRIEF DESCRIPTION OF THE DRAWINGS

FIG. 1B shows a partial side view of an exemplary phantom design in accordance with the present invention.

FIG. 1D shows a partial top-down view of an exemplary phantom design in accordance with the present invention.

DETAILED DESCRIPTION

Figure 1A:
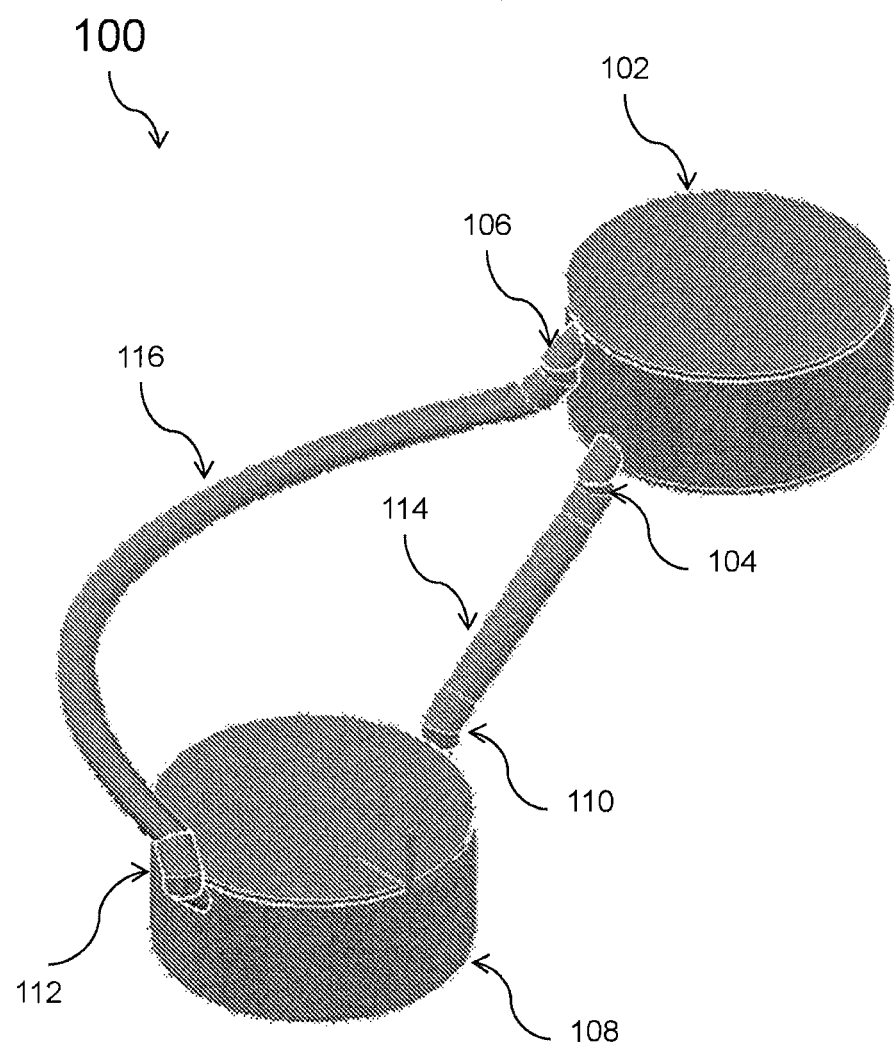
FIG. 1A shows a partial isometric view of an exemplary phantom design in accordance with the present invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, commercially available phantoms typically require a motor and external power for operation can be bulky, expensive, or require lengthy set-up times. Therefore, the present invention overcomes these limitations by providing a reliable phantom that does not require external power for operation, that is compact, that can be manufactured for a relatively low cost, and can be simple to setup and use.

Figure 1C:
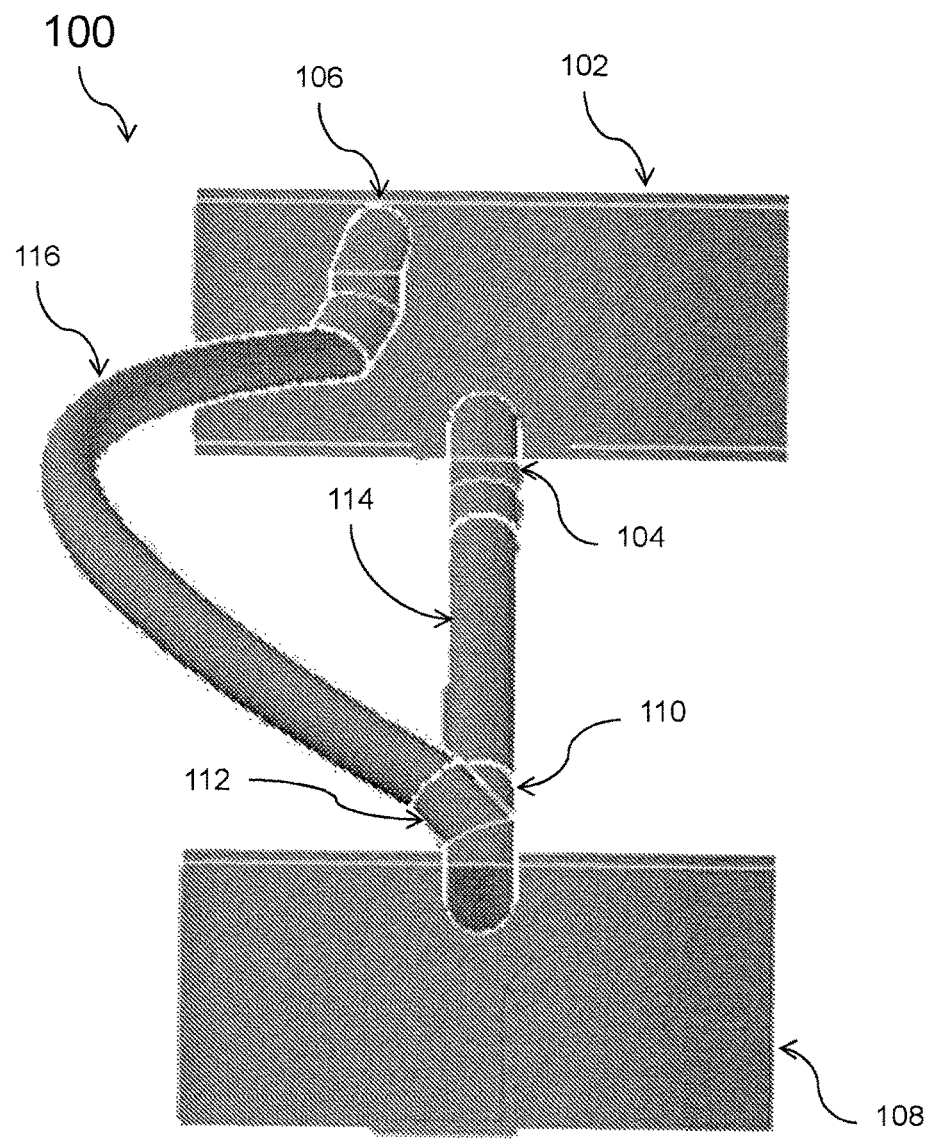
FIG. 1C shows a partial front view of an exemplary phantom design in accordance with the present invention.

Turning first to FIGS. 1A-1D and FIGS. 2A-2D, an exemplary phantom design in accordance with the present invention is shown. FIG. 1A shows a partial isometric view of this exemplary phantom design, FIG. 1B shows a partial side view of this exemplary phantom design, FIG. 1C shows a partial front view of the exemplary phantom design, and FIG. 1D shows a partial top-down view of the exemplary phantom design.

As shown in FIGS. 1A-1D, the phantom 100 includes a first reservoir 102 with a first fluid port 104 and a first pressure port 106. The phantom 100 also includes a second reservoir 102 with ports with a second fluid port 110 and a second pressure port 112.

The phantom 100 further includes a fluid line 114 connecting the first fluid port 104 and second fluid port 110 so that the interior of the first reservoir 102 and the second reservoir 108 are connected via fluid line 114. The phantom 100 also includes a pressure line 116 connecting the first pressure port 106 and second pressure port 112 so that the interior of the first reservoir 102 and the second reservoir 108 are also connected via pressure line 116.

Although not shown for clarity, the phantom 100 would also include at least one tissue mimicking material formed at least around fluid line 115. However, the tissue mimicking material can surround all the components illustrated in FIGS. 1A-1D. The mimicking material can be of sufficient strength to support the components illustrated in FIGS. 1A-1D and to maintain them in the relative positions shown in FIGS. 1A-1D. Alternatively or in combination with the mimicking material, the lines 114 and 116 can be of a sufficient stiffness to maintain the relative positions shown in FIGS. 1A-1D. However, in still other embodiments, additional structural support features (not shown) can also be incorporated into the phantom to support and maintain the relative position of the various components illustrated in FIGS. 1A-1D.

Figure 2A:
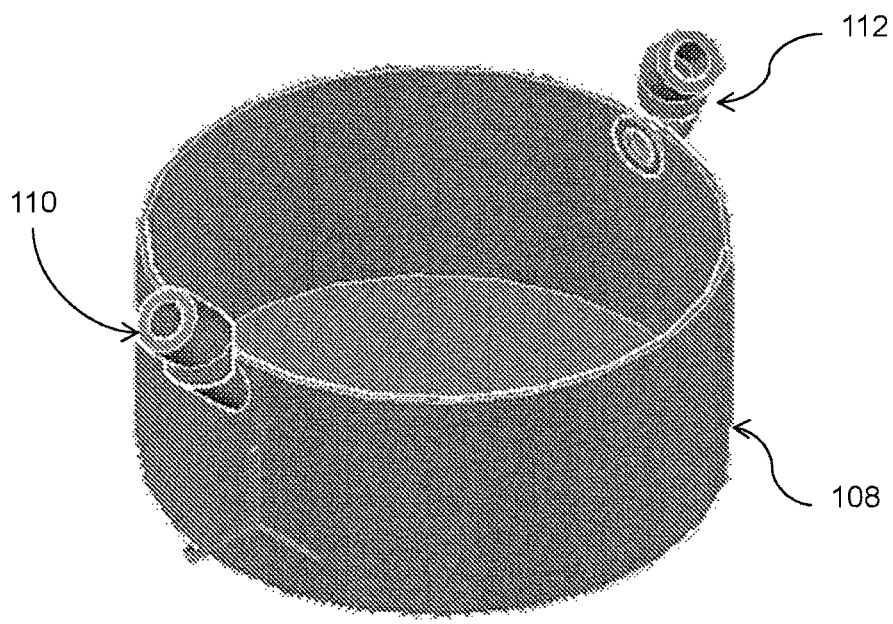
FIG. 2A shows a partial isometric view of a first reservoir of the exemplary phantom design of FIGS. 1A-1D.
Figure 2B:
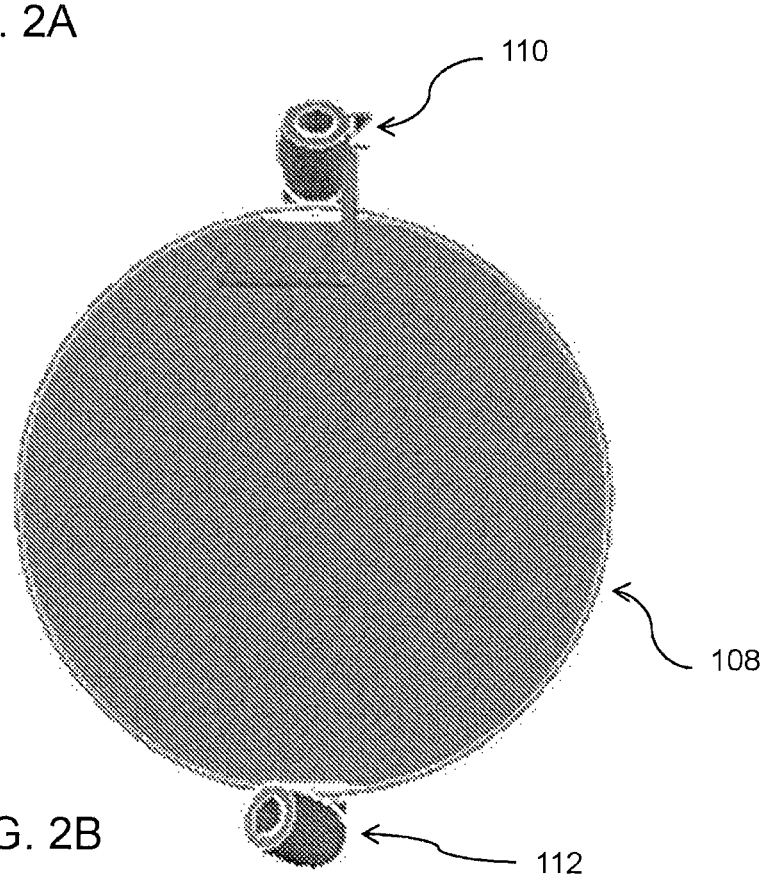
FIG. 2B shows a partial top-down view of a first reservoir of the exemplary phantom design of FIGS. 1A-1D.
Figure 2C:
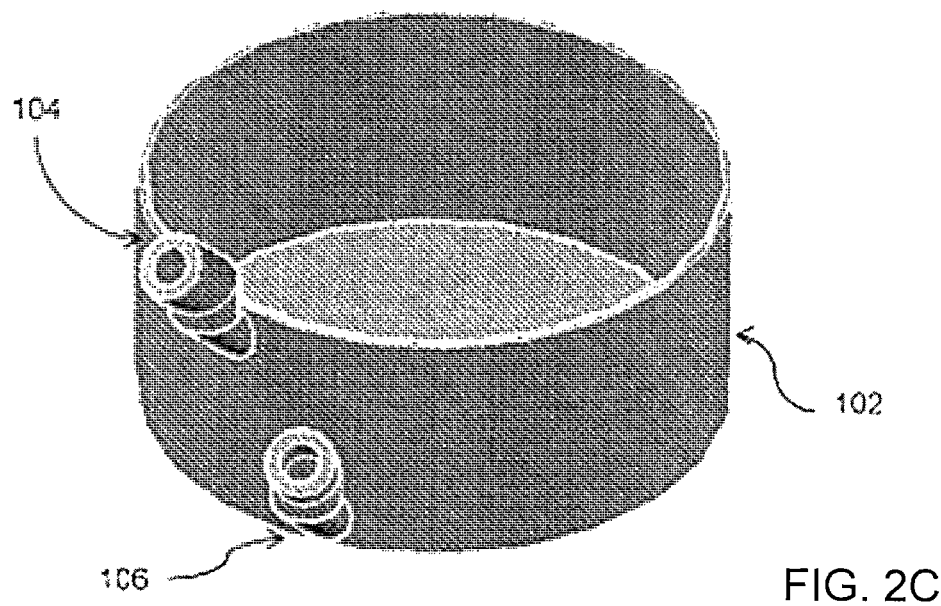
FIG. 2C shows a partial isometric view of a first reservoir of the exemplary phantom design of FIGS. 1A-1D.
Figure 2D:
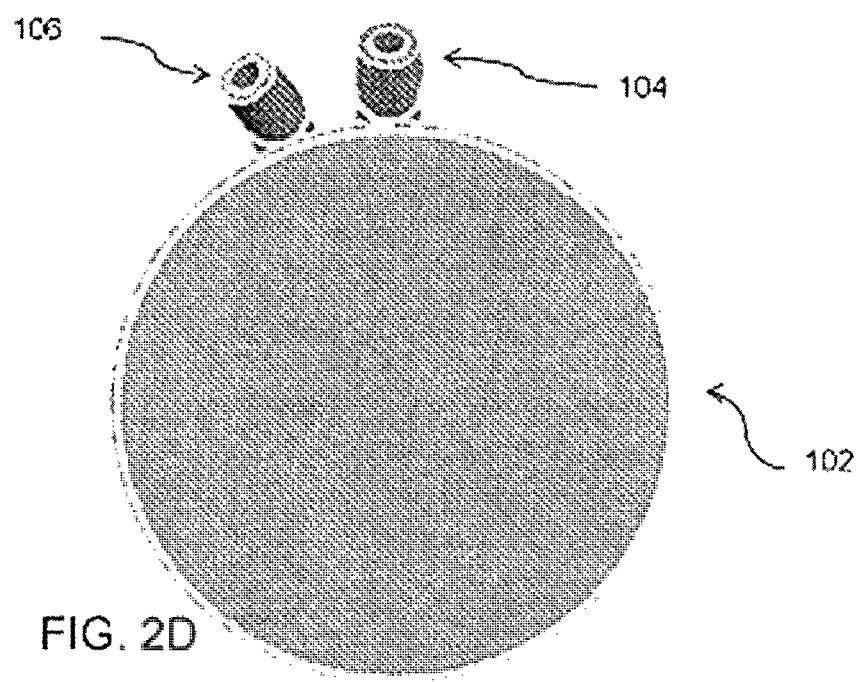
FIG. 2D shows a partial top-down view of a first reservoir of the exemplary phantom design of FIGS. 1A-1D.

A more detailed view of the reservoirs 102, 108 and ports 104, 106, 110, 112 is shown in FIGS. 2A-2D. FIG. 2A shows a partial isometric view of the second reservoir 108 and FIG. 2B shows a partial top-down view of the second reservoir 108. Similarly, FIG. 2C shows a partial isometric view of the first reservoir 102 and FIG. 2D shows a partial top-down view of the first reservoir 102.

In some cases, turbulent flow of liquid or gas can cause inconsistent flow of fluid through the fluid line 114. Accordingly, the various components can be designed to reduce turbulence. For example, the components described herein can have reduced interior surface roughness to reduce turbulence. In another example, the components can also be structurally reinforced to reduce vibrations. In still another example, turbulence-reducing features can be incorporated into some components, including, but not limited to: flow straighteners or honeycombed segments, meshes, porous media, or fibers. However, the invention is not limited to any particular method and any other methods of reducing turbulence can be used.

As shown in FIGS. 1A-1D and 2A-2D, the phantom 100 consists of a pair of short, substantially cylindrical reservoirs with a particular placement of ports. In reservoir 102, the first fluid port 104 and the first pressure port 106 are positioned at or near the opposite ends of the cylinder forming reservoir 102. In reservoir 108, the second fluid port 110 and the second pressure port 112 are positioned at or near the same end of the cylinder forming reservoir 108. However, the various embodiments are not limited in this regard. In other embodiments, the reservoirs can have any other shapes. One alternate design is illustrated by phantom design 300 in FIGS. 3A and 3B.

Figure 3A:
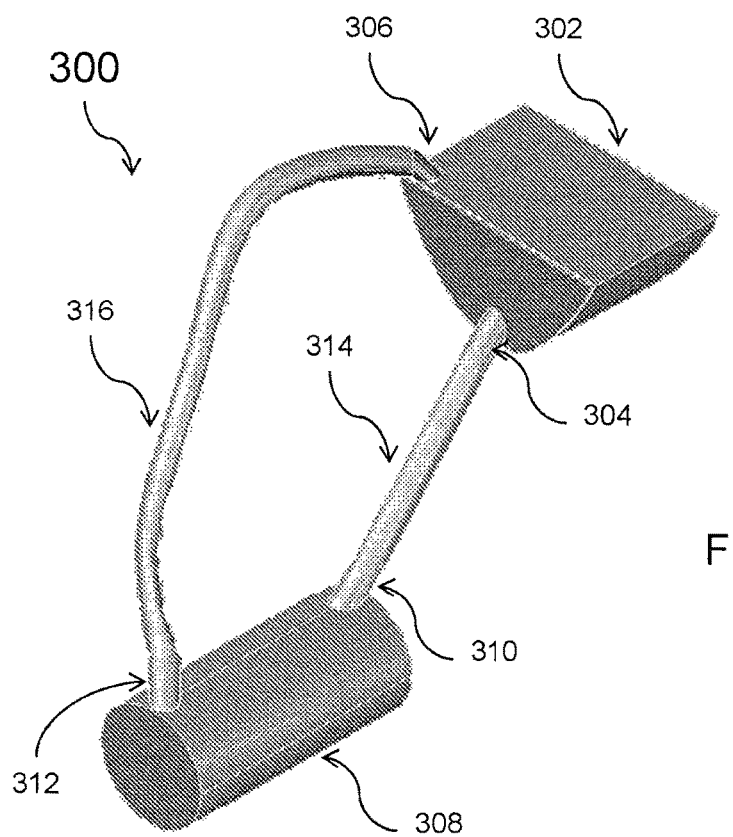
FIG. 3A shows a partial isometric view of an exemplary phantom design in accordance with the present invention.
Figure 3B:
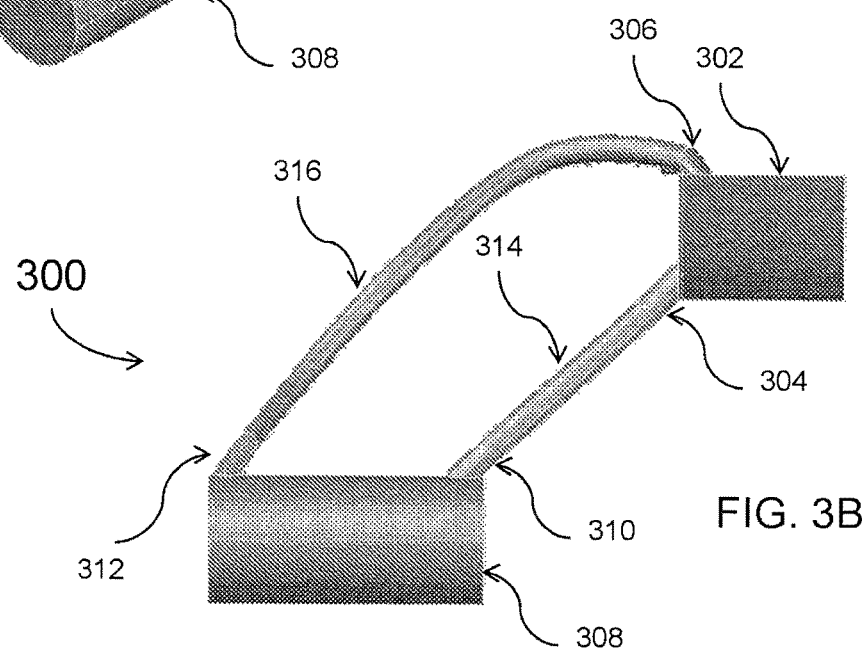
FIG. 3B shows a partial side view of an exemplary phantom design in accordance with the present invention.

FIG. 3A shows a partial isometric view of this second exemplary phantom design and FIG. 3B shows a partial side view of this exemplary phantom design.

Similar to the phantom design 100 in FIGS. 1A-1D, the phantom 300 includes a first reservoir 302 with a first fluid port 304 and a first pressure port 306. The phantom 300 also includes a second reservoir 302 with ports with a second fluid port 310 and a second pressure port 312.

The phantom 300 further includes a fluid line 314 connecting the first fluid port 304 and second fluid port 310 so that the interior of the first reservoir 302 and the second reservoir 308 are connected via fluid line 314. The phantom 300 also includes a pressure line 316 connecting the first pressure port 306 and second pressure port 312 so that the interior of the first reservoir 302 and the second reservoir 308 are also connected via pressure line 316.

However, unlike phantom 100, the reservoirs of phantom 300 are designed an arranged differently. For example, reservoir 302 is substantially a half-cylinder with the first fluid port 304 positioned at or near the circumference of the half-cylinder and the first pressure port 306 are positioned at or near the "cutline" for the half-cylinder. In reservoir 308, the second fluid port 304 and the first pressure port 306 are positioned at opposite ends of the cylinder forming reservoir 308.

Figure 4:
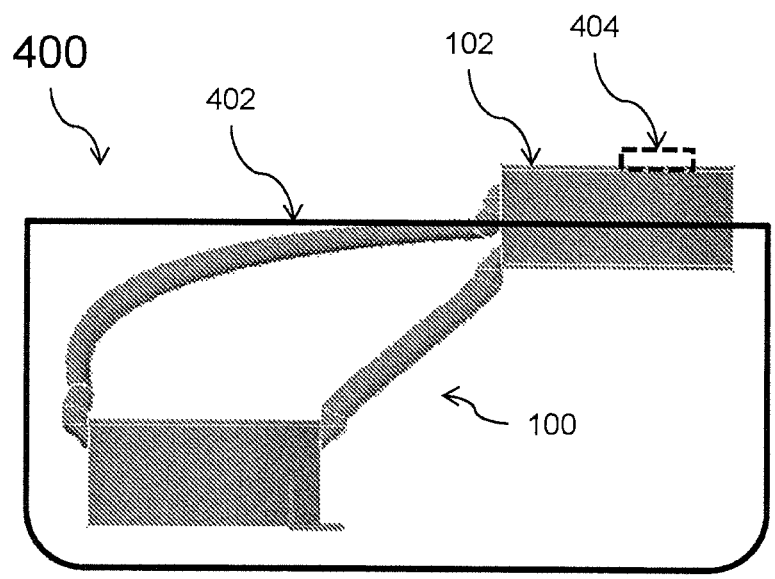
FIG. 4 shows a side view of an exemplary phantom design in accordance with the present invention.
Figure 5:
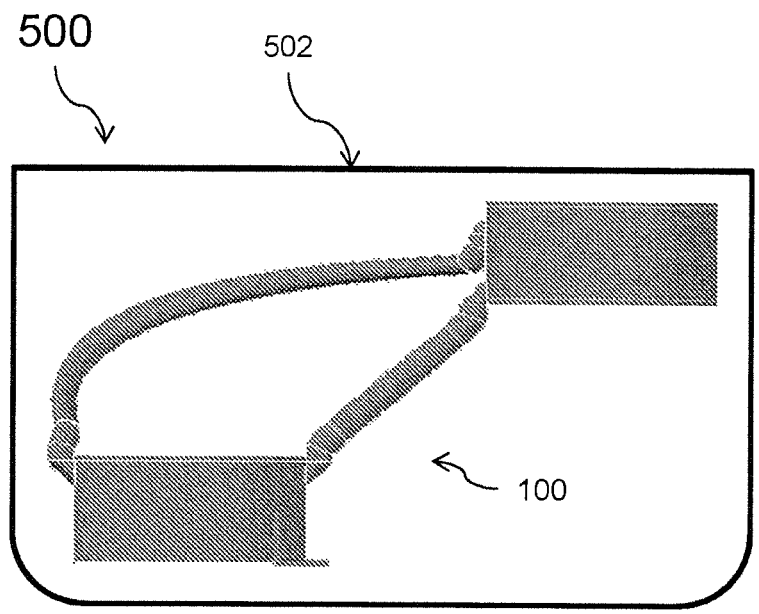
FIG. 5 shows a side view of another exemplary phantom design in accordance with the present invention.

Now turning to FIGS. 4 and 5, there are shown two exemplary arrangements for the mimicking material relative to the other components of the phantom. For ease of illustration, the arrangement of the mimicking material relative to the components is FIGS. 1A-1D is shown. FIG. 4 shows an exemplary configuration of a phantom 400 in which at least one portion of reservoir 102 remains outside of the mimicking material 400. FIG. 5 shows an exemplary configuration of a phantom 500 in which all components are surrounded by the mimicking material 502.

Although the configuration of phantom 500 can be used for a wide range of testing, it is possible that in some cases the testing needed can require different fluids to be tested. Alternatively, the fluid used for testing may degrade over time. In such circumstances, it may be desirable to have the ability to replace the fluid. The configuration of phantom 400 can be used to provide such capabilities. As shown in FIG. 4, the exposed reservoir, reservoir 102, can be configured with an access port 404 to allow the fluid in phantom 400 to be replaced or replenished as needed. The access port 404 can be configured to be resealed so as to not allow fluid to escape one replenished.

Figure 6:
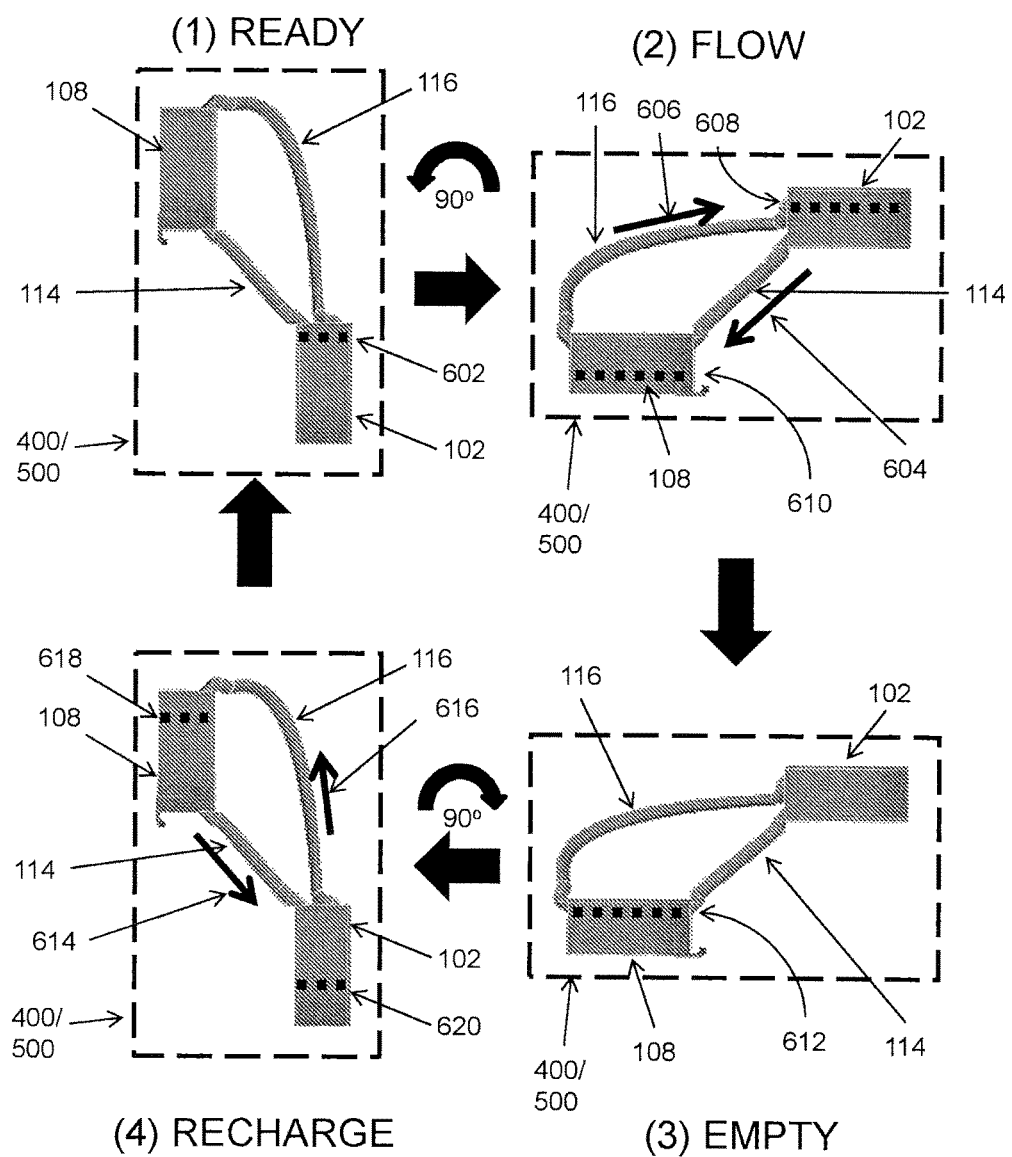
FIG. 6 schematically illustrates the use of a phantom in accordance with the present invention.

Now that a basic configuration a phantom in accordance with the various embodiments has been described, a more detailed discussion of the configuration and operation of the phantom and its various components is now provided with respect to FIG. 6.

FIG. 6 illustrates the operational cycle for a phantom in accordance with the various embodiments. As shown in FIG. 6, a phantom configured in accordance with the various embodiments, such as phantom 400 or 500, can be operated through four steps (READY, FLOW, EMPTY, RECHARGE) by merely repositioning or reorienting the phantom into one of two positions.

In a first position, the phantom is positioned such that a first reservoir 102 is positioned vertically above the second phantom 104. This is the position illustrated in the FLOW and EMPTY steps. In a second position, the phantom is positioned such that the second reservoir 108 is positioned vertically above the first phantom 102. This is the position illustrated in the RECHARGE and READY steps. This configuration is provided so that when in either position, gravity causes fluid in elevated reservoir to flow to the lower reservoir.

Further, the positions of the ports are selected so that the flow of fluid is unimpeded by air pressure. In particular, the fluid ports are oriented such that an elevated reservoir empties from a fluid port positioned at or near the bottom of the elevated reservoir (with respect to gravity) and fills the other reservoir via a fluid port at the top of the other reservoir. Further, the path of fluid between the reservoirs (i.e., the path of fluid through the fluid ports and the fluid line 114) is arranged such that the flow of fluid is always downward (with respect to gravity).

Further, to ensure a predictable flow of fluid between reservoirs, any gas in the reservoir being filled is transferred to the elevated reservoir via the pressure line 116. For the pressure line 116, the pressure ports are arranged so that the pressure ports are at or near the top of each reservoir (with respect to gravity). In this way, a pressure build-up against fluid in the fluid line 114 is avoided.

The operation of flows of fluid and gas will now be explained with respect to FIG. 6. The cycle of FIG. 6 can begin at the READY state where the fluid is located solely in one reservoir. For example, as shown in FIG. 6, the second reservoir 108 is the elevated reservoir and all fluid has been transferred to the first reservoir 102, as indicated by dotted line 602.

When the phantom 400 or 500 is ready to be used, it can be repositioned in the FLOW state, as shown in FIG. 6. In particular, the phantom 400 or 500 is rotated 90 degrees so that the first reservoir 102 becomes the elevated reservoir and fluid begins to flow 604 down to the second reservoir 108 via fluid line 114. In this manner the fluid in first reservoir 102 (indicated by 608) is transferred to second reservoir 108 (indicated by 610). To ensure uninterrupted flow, any gas in second reservoir 108 is transferred via pressure line 116 to first reservoir 102. In particular, a gas flow 606 is provided a path through the top of second reservoir 108 to the top of first reservoir 102. In this way, there is no gas pressure that accumulates against fluid being delivered via the fluid line 114. This process then continues until the phantom 400 or 500 the reaches the EMPTY state, where all the fluid in the first reservoir 102 is transferred to the second reservoir 108 (as indicated by 612).

Thereafter, to refill the first reservoir, the phantom 400 or 500 can be repositioned in the RECHARGE state, as shown in FIG. 6. That is, the phantom 400 or 500 can be rotated back 90 degrees so that the second reservoir 108 becomes the elevated reservoir and fluid begins to flow 614 down to the first reservoir 102 via fluid line 114. In this manner the fluid in second reservoir 108 (indicated by 618) is transferred to first reservoir 108 (indicated by 620). As with the FLOW step, any gas in first reservoir 102 is transferred via pressure line 116 to second reservoir 108 to ensure uninterrupted flow. In particular, the gas is provided a path through the top (with respect to gravity) of first reservoir 104 to the top (with respect to gravity) of second reservoir 108. In this way, there is no gas pressure that accumulates against fluid being delivered via the fluid line 114. This process then continues until the phantom 400 or 500 the reaches the READY state, where all the fluid in the second reservoir 102 is transferred to the first reservoir 102 (as indicated by 602).

It should be noted that the RECHARGE and READY states can also be considered to be FLOW and EMPTY states, respectively. That is, the phantom could be designed for use when fluid is flowing in either direction through fluid line 114. In such configurations, the path between the reservoirs can be configured to be symmetric or asymmetric. That is, the flow in each direction can be the same or different. In the case of the latter, the asymmetric configuration may be desired to allow Doppler testing at different flows.

In some configurations, one or more control valves or similar devices can be used to control the flow of liquid.

Such devices can be located along the fluid line, the pressure line or both. That is, since the reservoirs and lines form a closed system, controlling flow along either the pressure line or the fluid line will effect a change in flow. In fact, such devices can even be used to shut off flow completely.

It should also be noted that although the phantom illustrated here includes only a single fluid line and a single pressure line, the various embodiments are not limited in this regard. In some configurations, there may be multiple fluid lines, multiple pressure lines or both. Further in other configurations, multiple selectable lines can be provided. That is, one or more valves or other flow control mechanisms can be provided to allow a user to select which fluid lines to allow liquid to flow through. Similarly one or more control valves can also be provided to adjust the flow amongst the various lines.

It should also be noted that in some embodiments, it may be desirable to maintain the gas separate from the fluid. Thus, in some configurations each reservoir may include a bladder to separate the gas from the fluid. Accordingly, one bladder drains into another during use of the phantom.

Further, it should also be noted that the phantom can be made in a number of sizes, with design changes to give higher or lower velocities of fluid. The velocity depends on the height of the fluid in the reservoir, the cross-sectional area of the elevated reservoir, as well as the cross-sectional area of the draining port of that reservoir. The following equation describes relationships using cylindrical reservoirs.

$$v \propto \left(\frac{A_2}{A_1}\right) \times \sqrt{h}$$

where v is fluid velocity exiting the reservoir, $A_1$ and $A_2$ are the cross sectional areas of the reservoir and the exit ports respectively, and h is the height of the fluid in the reservoir. Thus, by adjusting these values, almost any velocity within reason could be represented in the phantom design, making this design concept versatile for a number of testing purposes.

EXAMPLES

The examples shown here are not intended to limit the various embodiments. Rather they are presented solely for illustrative purposes.

Test Phantom 1—Methods and Testing

Figure 7:
FIGS. 7 and 8 show an phantom fabricated in accordance with the present invention before and after the addition of tissue mimicking material, respectively.
Figure 8:
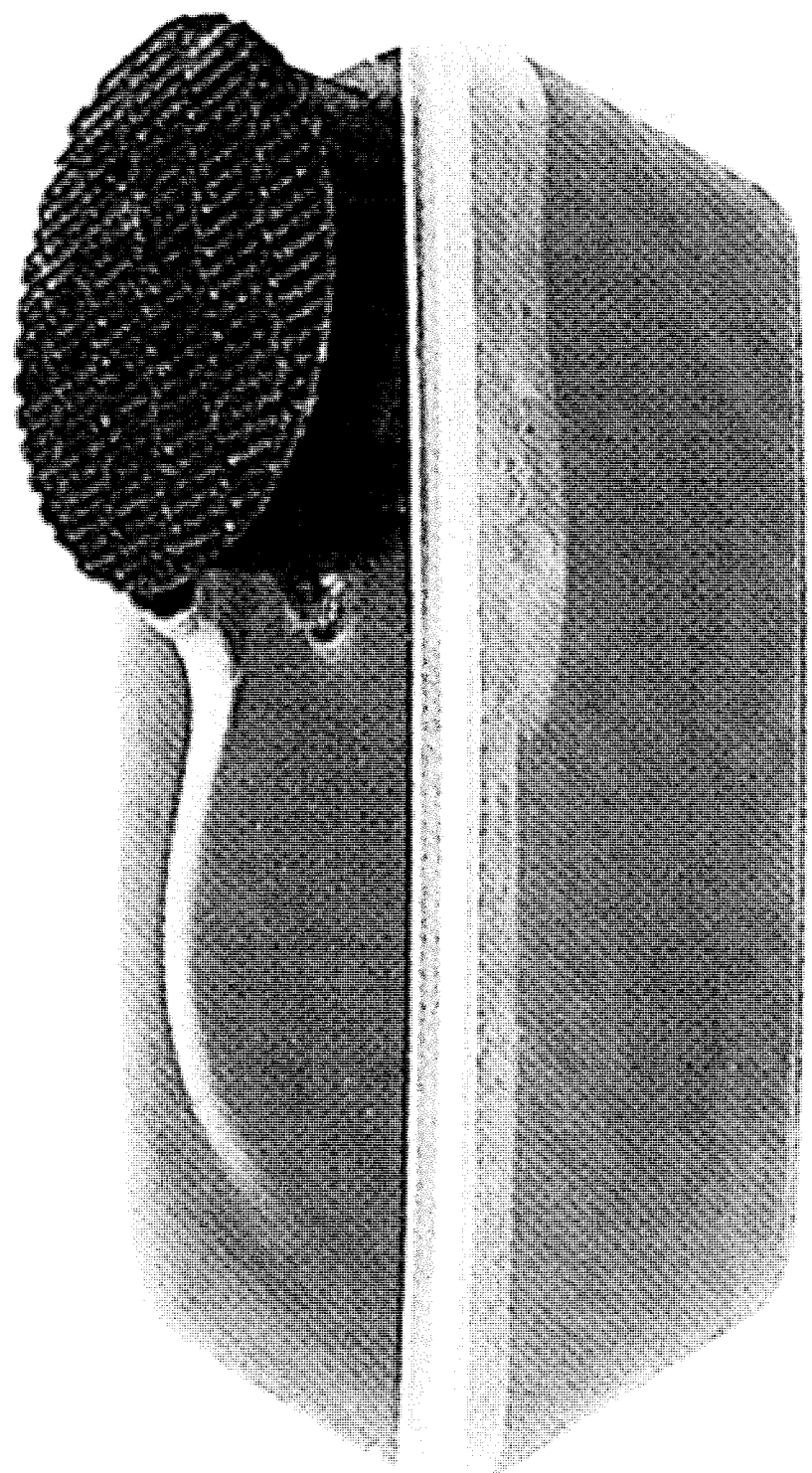

One phantom was designed in AutoDesk's AutoCAD program (AutoDesk, San Rafael, Calif.) and fabricated in the 70 laboratory using a 3D printer. The basic design of the phantom consists of two reservoirs with two connecting tubes between the two reservoirs, as described above with respect to FIGS. 1A-1D and 2A-2D. The constructed phantom is shown in FIGS. 7 and 8, which show the phantom before and after the tissue mimicking material is added.

As already described above, fluid flow is initiated by changing the orientation of the phantom. Specifically, fluid flows either from reservoir when the phantom is flipped 90 degrees as discussed above.

For this phantom, the reservoirs were fabricated using a MakerBot Replicator2 3D printer (MakerBot Industries, LLC. Brooklyn, N.Y.). The reservoirs were created using polylactic acid as the printing material. A quarter-inch inner diameter latex tubing was used to connect the reservoirs for fluid flow and air return. The reservoir system once assembled was filled with a Doppler test fluid (ATS Laboratories, Inc. Bridgeport, Conn.). This fluid is a glycerol solution that contains polyamide particles averaging 30 micrometers in size. After sealing, the entire reservoir system was seated in a gelatin-based tissue-mimicking material The reservoirs were placed in a container and glued to the bottom, maintaining the synthetic vessel at a 45 degree angle. The tissue mimicking material, while warm enough to maintain its liquid form, was then poured around the sealed reservoir system and allowed to cool and congeal into a solid. This method of seating the phantom has resulted in good acoustic coupling of the vessel to the gel. The surface of the tissue mimicking material was set even with the highest point of the synthetic vessel, which varies in depth from 0 to about 4 cm. All measurements were taken at 2 cm depth in this study.

Once assembled, the phantom can be scanned using any of the conventional Doppler modes, e.g. color Doppler or spectral Doppler. To achieve a more consistent and reproducible result than can generally be obtained with a hand-held ultrasound probe, a transducer clamp is used to secure the ultrasound probe to the surface of the phantom during measurement. During testing it was found that consistent probe placement was very important.

Figure 9:
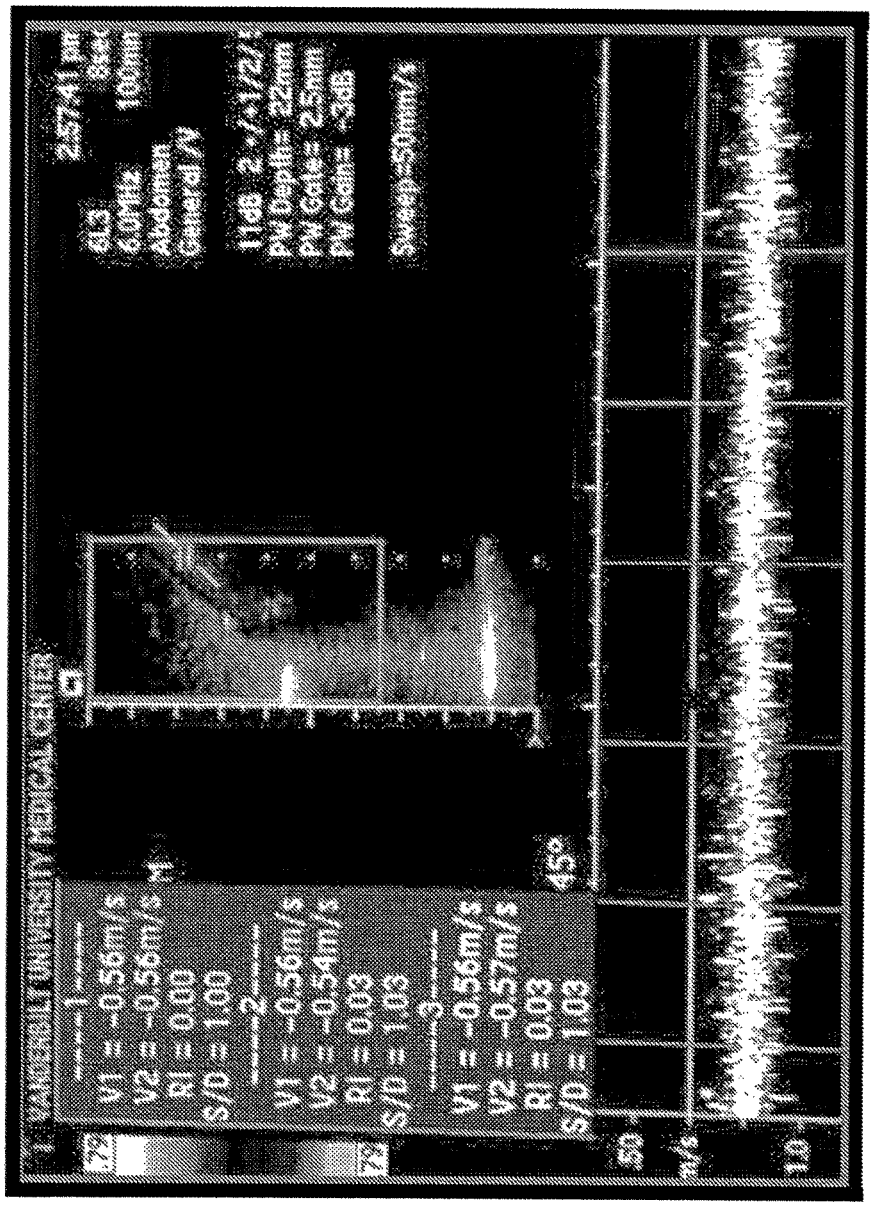
FIG. 9 shows Doppler results for the phantom of FIGS. 7 and 8.

After the phantom was constructed, it was tested for variations in spectral data collection and the mean velocity generated in the phantom was measured using a non-ultrasound technique. The ultrasound system used in testing was an Acuson Sequoia with a 6L-3 linear probe (Siemens Medical Solutions, Malvern, Pa.). Testing consisted of repeated phantom runs in which the Doppler spectrum was obtained from a manually positioned sample volume approximately centered within the lumen of the latex tubing. FIG. 9 shows the Doppler image of the phantom and corresponding Doppler spectrum.

The mean velocity of the fluid flow generated in the phantom was independently determined by deconstructing the phantom and allowing the phantom to drain into a graduated cylinder. Since the phantom was sealed at atmospheric pressure and the synthetic vessel was cut at the point at which it met the bottom reservoir, it was assumed that no significant change in flow impedance occurred. To evaluate the volumetric flow rate, the top reservoir was mounted above a graduated cylinder. Then, the synthetic vessel was clamped off and the reservoir filled with the same Doppler test fluid. A high speed camera at 240 frames/sec was set up to visualize the fluid level rising in the graduated cylinder. The clamp was released and the rising fluid level in the cylinder over time was captured and reviewed frame by frame.

The volumetric flow rate was determined to be the volume of Doppler fluid flowing into the graduated cylinder per unit time (cm3/sec). Using the measured volumetric flow rate and the known cross-sectional area (cm2) of the latex tube draining a fluid, an average velocity (cm/sec) was calculated by dividing the flow rate by the tube's cross-sectional area.

Test Phantom 1—Results

Figure 10:
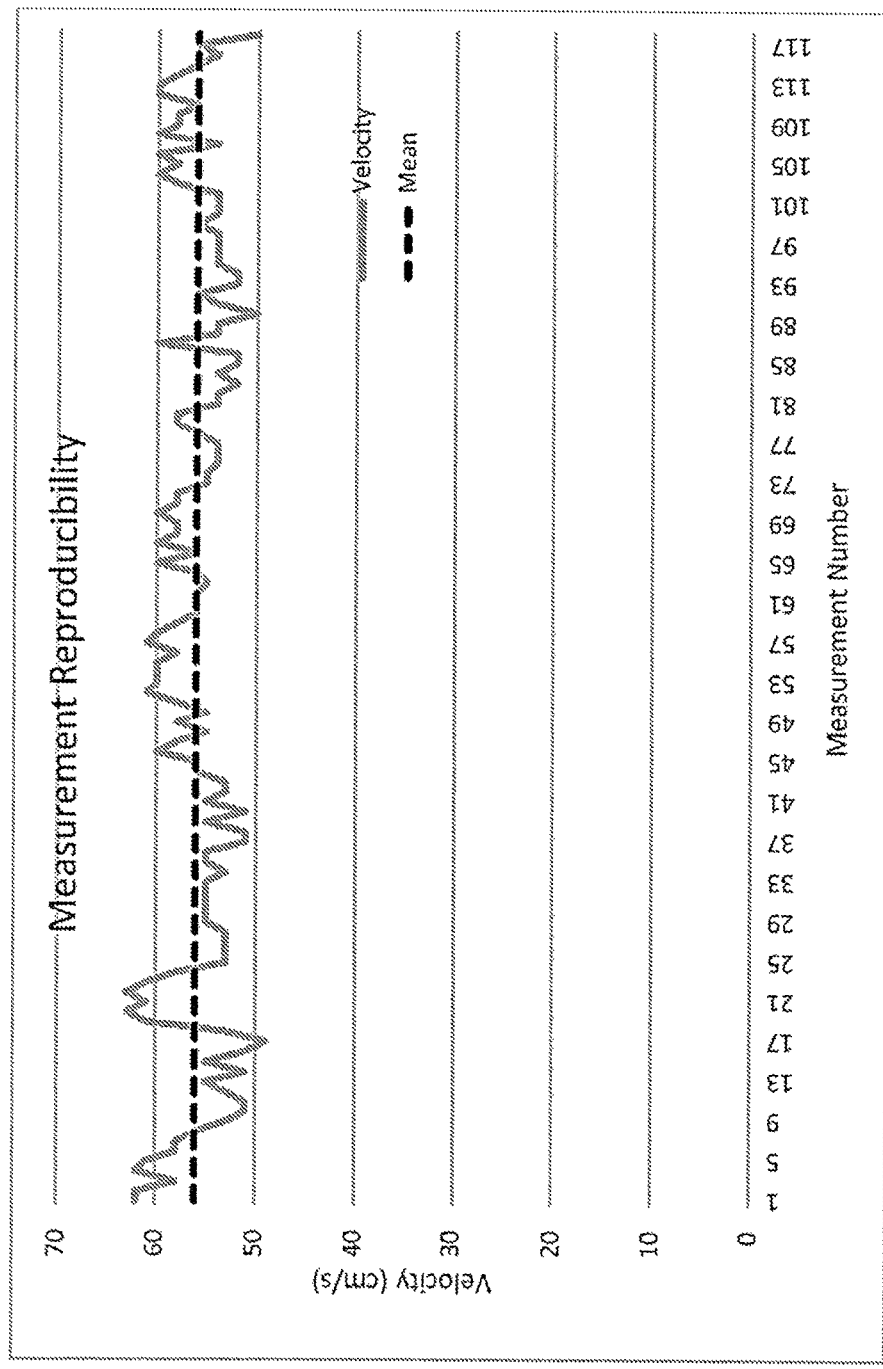
FIG. 10 shows average velocity measurements for the phantom of FIGS. 7 and 8.

The measured variability in Doppler flow velocity was evaluated from measurements made with the Acuson Sequoia. These results are shown in FIG. 10, which shows a plot of flow velocity for all measurements and the mean. The mean value of these 130 measurements was 56 cm/s. The standard deviation of measurements was 3.2 cm/s and the coefficient of variation was 0.06 cm/s.

The calculation of the mean velocity derived from the measured volumetric flow rate yielded a mean value of 51.9 cm/s with a standard deviation of 0.7 cm/s over the 4 measurements. Thus for the Sequoia system tested, it was determined that the system was accurate within 10% of the mean velocity estimated using the graduated cylinder. There is some inherent error in the measurements of the Doppler waveform that comes from the user-placed sample volume. Because the gate sample volume is smaller than the diameter of the synthetic vessel, the camera-based flow rate measurements do not compare directly, though as expected for the measurement from a volume smaller than the vessel, the Doppler measurements have a higher indicated velocity. Other effects that may contribute error to the Doppler measurement, like spectral broadening, were not characterized explicitly for this study, but may also contribute to error in this comparison.

Test Phantom 2—Methods and Testing

Figure 11:
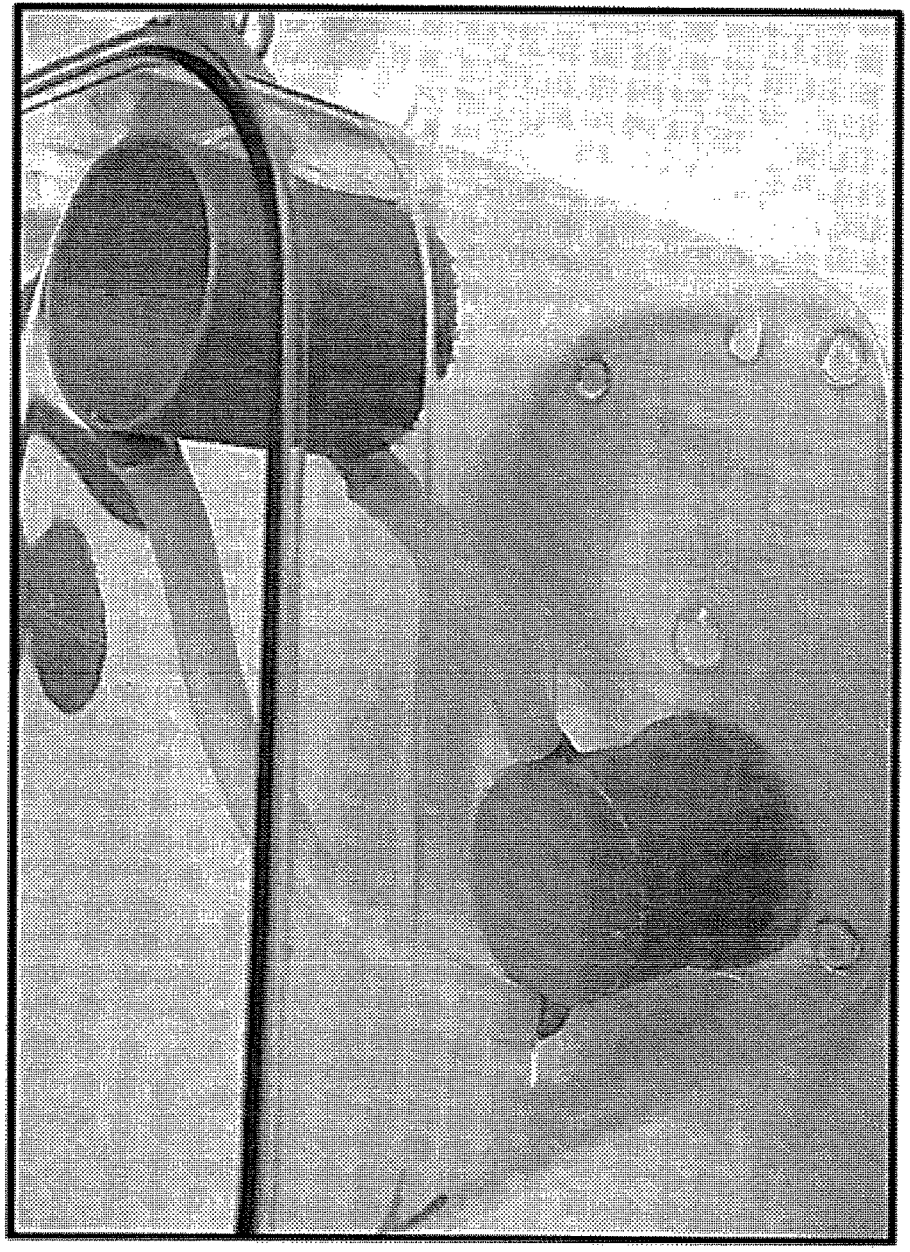
FIG. 11 shows another phantom fabricated in accordance with the present invention before the addition of tissue mimicking material.

Another phantom was prepared and fabricated in substantially the same way as the first phantom discussed above. FIG. 11 shows the phantom prior to adding the tissue mimicking material. The design varies primarily with respect to the size and shape of the reservoirs, which are more elongate in this configuration. However, this phantom was operated in substantially the same way.

Figure 12:
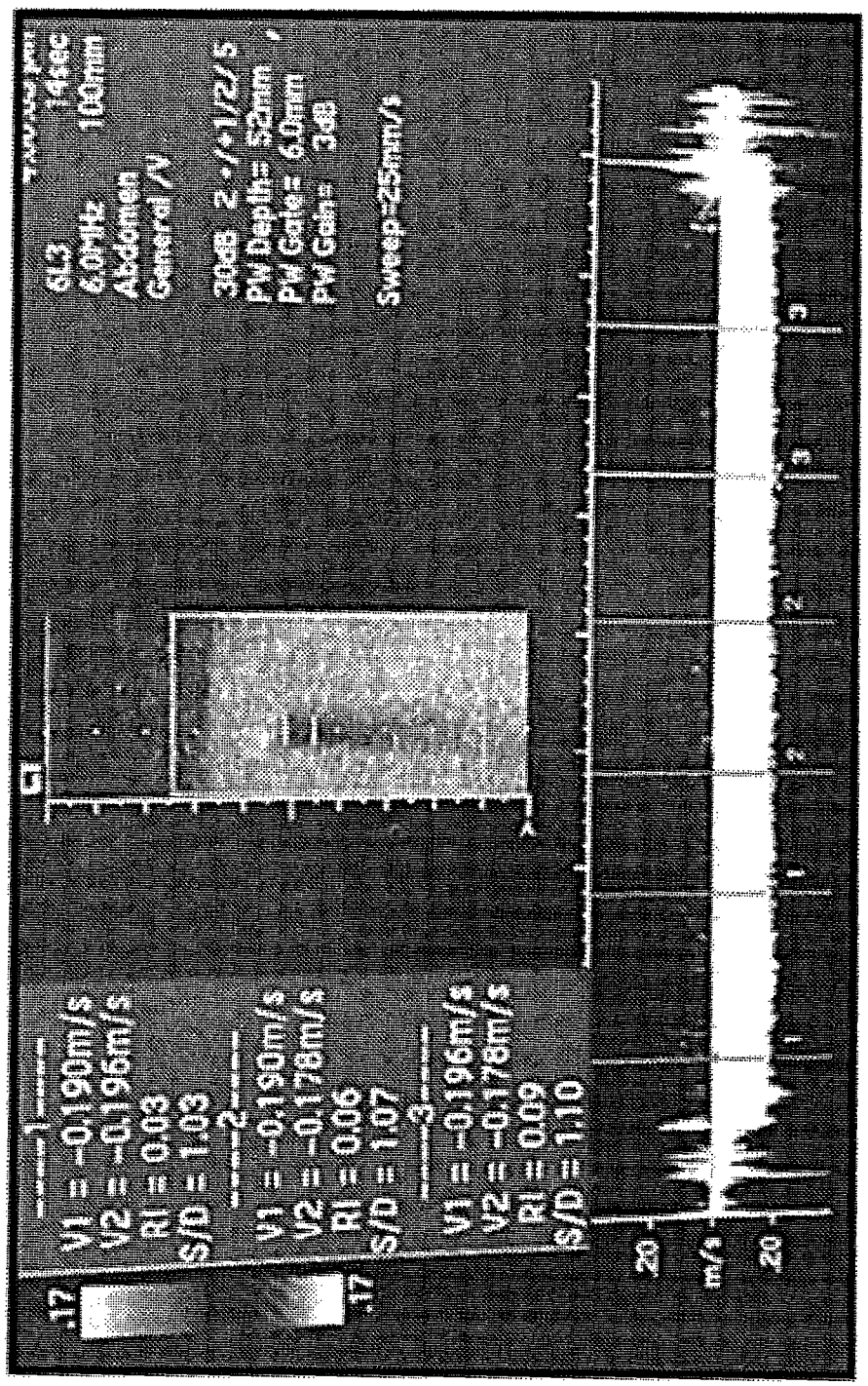
FIGS. 12, 13, and 14 show Doppler results for the phantom of FIG. 11.
Figure 14:
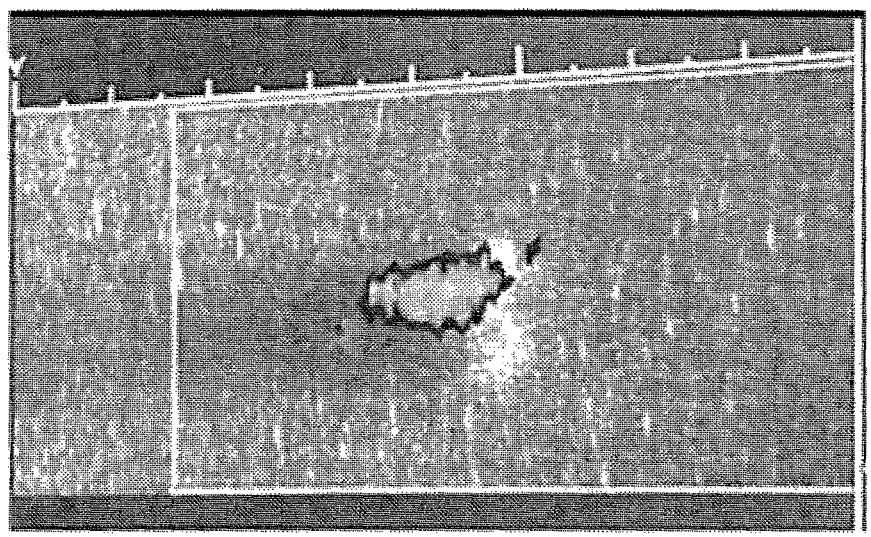
Figure 13:
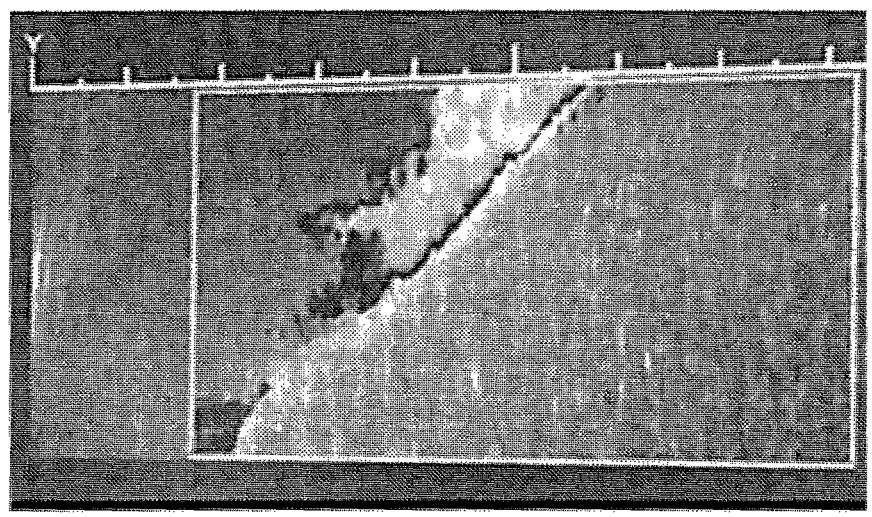

FIG. 12 shows velocity data acquired from the phantom in pulsed Doppler mode. FIGS. 13 and 14 qualitatively displays laminar flow in the tube. These results are substantially similar to those of the previous phantom configuration.

DISCUSSION

The test phantoms demonstrate a phantom that can provide rapid and convenient assessment of stability and variation of a Doppler ultrasound system. The phantom design of the various embodiments provides an absolute fluid-flow velocity that is within the range of relevant blood velocities in the human body. It is possible that some gas bubbles could be incorporated into the fluid over time, which could yield greater variability. However, providing a means to replace the fluid, as discussed with respect to FIG. 4, can address such issues.

Further, it has been demonstrated that this phantom design would be useful for obtaining measurements of mean velocity estimation as described earlier and flow direction by using color Doppler while draining the phantom in both directions. Angle correction software accuracy, which would be implicitly tested with the mean velocity estimation, could also be evaluated. These parameters can be characterized by this phantom.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A Doppler phantom comprising:
a first reservoir;
a second reservoir;
a fluid line coupling the first reservoir and the second reservoir;
a pressure line coupling the first reservoir and the second reservoir; and
a tissue mimicking material surrounding at least the fluid line;
wherein the phantom can be positioned in at least a first position and a section position, wherein the first reservoir defines an elevated reservoir and the second reservoir defines a lower reservoir in the first position, wherein the second reservoir defines the elevated reservoir and the first reservoir defines the lower reservoir in the second position, wherein the fluid line defines a path for fluid to travel from the elevated reservoir to the lower reservoir in either of the first position or the second position, and wherein the pressure line defines a path for gas to transfer from the lower reservoir to the elevated reservoir while the fluid travels in either of the first position or the second position, and wherein the fluid travels in either of the first position or the second position exclusively via gravity.

2. The phantom of claim 1, wherein each of the first reservoir and the second reservoir are substantially cylindrical and parallel with each other.

3. The phantom of claim 1, wherein each reservoir of the first reservoir and the second reservoir comprises a fluid port coupling the fluid line to each reservoir and a pressure port coupling the pressure line to each reservoir.

4. The phantom of claim 3, wherein the fluid port for each reservoir is arranged so as to be at a bottommost portion in the elevated reservoir with respect to gravity and at a topmost portion in the lower reservoir with respect to gravity.

5. The phantom of claim 3, wherein the pressure port for each reservoir is arranged so as to be at a topmost portion in the elevated reservoir with respect to gravity and at a topmost portion in the lower reservoir with respect to gravity.

6. The phantom of claim 1, wherein the fluid line is configured to travel a direct path between the first reservoir and the second reservoir.

7. The phantom of claim 1, wherein at least one of the first reservoir or the second reservoir comprises an access port.

8. The phantom of claim 7, wherein each of the first position and the second position comprises rotating the phantom by 90 degrees from another of the first position and the second position.

* * * * *